US00PP28084P2

(12) United States Plant Patent
Eveleens

(10) Patent No.: US PP28,084 P2
(45) Date of Patent: Jun. 6, 2017

(54) ***HYDRANGEA* PLANT NAMED 'HORTMADACE'**

(50) Latin Name: *Hydrangea macrophylla*
Varietal Denomination: HORTMADACE

(71) Applicants: Horteve Breeding BV, Aalsmeer (NL); Kolster Holding BV, Boskoop (NL)

(72) Inventor: Cornelis Pieter Eveleens, Aalsmeer (NL)

(73) Assignees: HORTEVE BREEDING BV (part interest), Aalsmeer (NL); KOLSTER HOLDING BV (part interest), Boskoop (NL)

( * ) Notice: Subject to any disclaimer, the term of this patent is extended or adjusted under 35 U.S.C. 154(b) by 53 days.

(21) Appl. No.: 14/757,047

(22) Filed: Nov. 12, 2015

(51) Int. Cl.
*A01H 5/02* (2006.01)

(52) U.S. Cl.
USPC ..... Plt./250

(58) Field of Classification Search
USPC ..... Plt./250
See application file for complete search history.

*Primary Examiner* — June Hwu
(74) *Attorney, Agent, or Firm* — Penny J. Aguirre

(57) ABSTRACT

A new cultivar of *Hydrangea macrophylla* named 'HORTMADACE' that is characterized by its globular shaped inflorescence, its medium sized inflorescences, its sterile flowers with sepals that are very dark pink-red in color with a sturdy substance.

2 Drawing Sheets

Botanical classification: *Hydrangea macrophylla.*
Varietal denomination: 'HORTMADACE'.

CROSS REFERENCE TO RELATED APPLICATIONS

This application is co-pending with U.S. Plant Patent Applications filed for a plant derived from the same breeding program that are entitled *Hydrangea* Plant Named 'HORTMANI' (U.S. Plant patent application Ser. No. 14/757,043).

BACKGROUND OF THE INVENTION

The present invention relates to a new and distinct cultivar of *Hydrangea macrophylla* and will be referred to hereafter by its cultivar name, 'HORTMADACE'. 'HORTMADACE' represents a new mophead type *Hydrangea*, a deciduous shrub grown for use as a landscape plant, potted plant and as a cut flower.

The new cultivar was derived from a controlled breeding program conducted by the Inventor in Boskoop, The Netherlands. The objective of the breeding program is to develop new cultivars of *Hydrangea* with good cut flower qualities with unique flower colors. The objective with this new cultivar was to obtain a plant with sturdy red flowers with good color retention as they mature.

The Inventor made a cross in May 2006 between unnamed and unpatented plants in the Inventor's breeding program; reference no. 03-059-18 as the female parent and reference no. 05-001-04 as the male parent. The Inventor selected 'HORTMADACE', in June 2013 as a single unique plant amongst the seedlings that resulted from the above cross.

Asexual propagation of the new cultivar was first accomplished by the Inventor by softwood stem cuttings in Boskoop, The Netherlands in August 2009. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'HORTMADACE' as a unique cultivar of *Hydrangea.*

1. 'HORTMADACE' exhibits globular shaped inflorescences.
2. 'HORTMADACE' exhibits medium sized inflorescences.
3. 'HORTMADACE' exhibits sterile flowers that are very dark pink-red in color.
4. 'HORTMADACE' exhibits sterile flowers with sepals that have a sturdy substance.

The female parent of 'HORTMADACE', reference no. 03-059-18, differs from 'HORTMADACE' in having sepals that are darker and redder in color and in having fewer inflorescences. The male parent of 'HORTMADACE', reference no. 05-001-04, differs from 'HORTMADACE' in having sterile flowers with sepals that are lighter pink in color with a weaker substance, and in having a taller plant height. 'HORTMADACE' can be most closely compared to the cultivars 'Kolmaru' (U.S. Plant Pat. No. 25,104) and 'Glowing Alps' (not patented). 'Kolmaru' is similar to 'HORTMADACE' in having foliage that is medium in size and in having a similar plant habit. 'Kolmaru' differs from 'HORTMADACE' in having sepals that are dark red in color, in having less globular shaped inflorescences and in having leaves that are darker green in color. 'Glowing Alps' differs from 'HORTMADACE' in having longer stem internodes lengths and in having inflorescences that are larger in size with sterile sepals that are more purple in color.

BRIEF DESCRIPTION OF THE DRAWINGS

The accompanying colored photographs illustrate the overall appearance and distinct characteristics of the new

*Hydrangea*, 'HORTMADACE'. The photographs were taken of a two year-old plant as grown in a greenhouse in a 1.5-liter container in Boskoop, The Netherlands.

Figure 1:
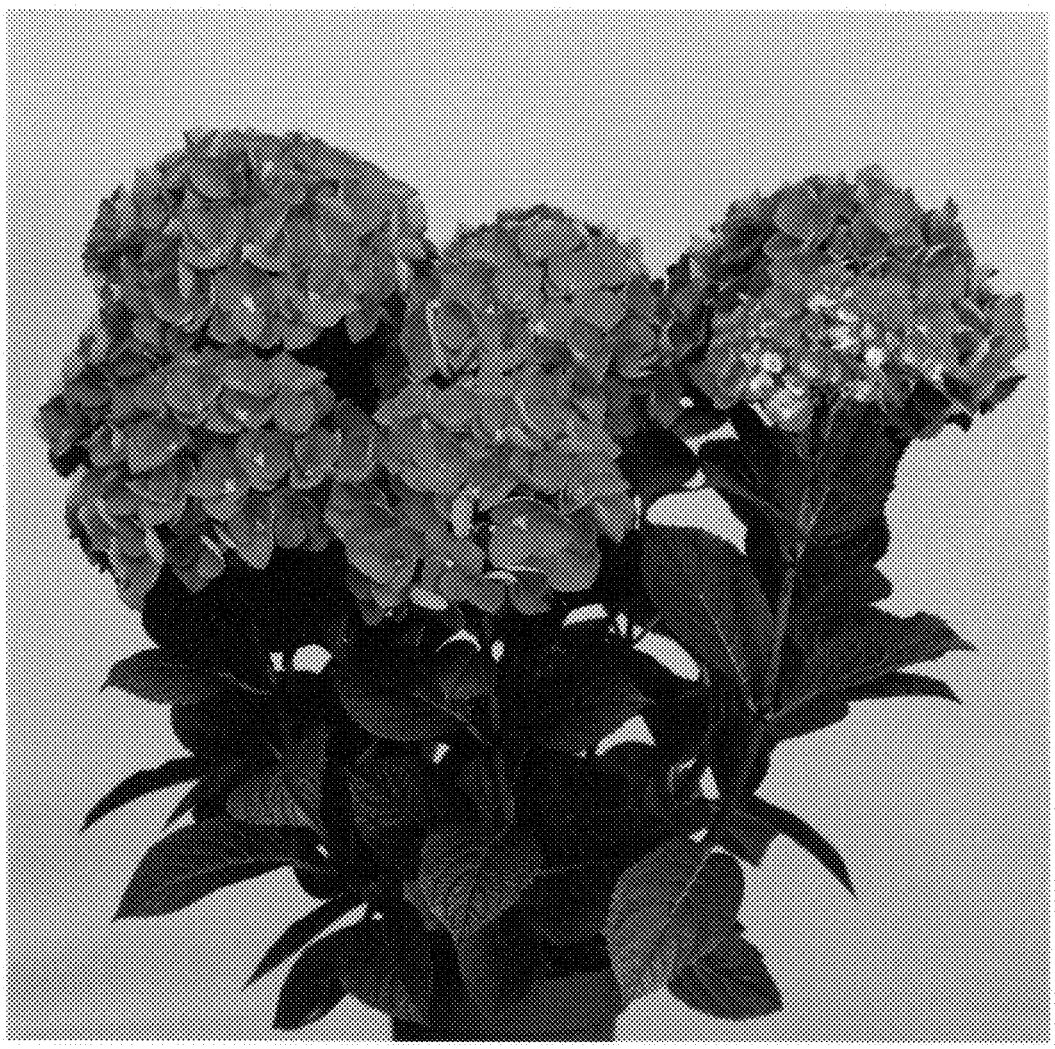

The photograph in FIG. 1 provides a side view of a plant of 'HORTMADACE'.

Figure 2:
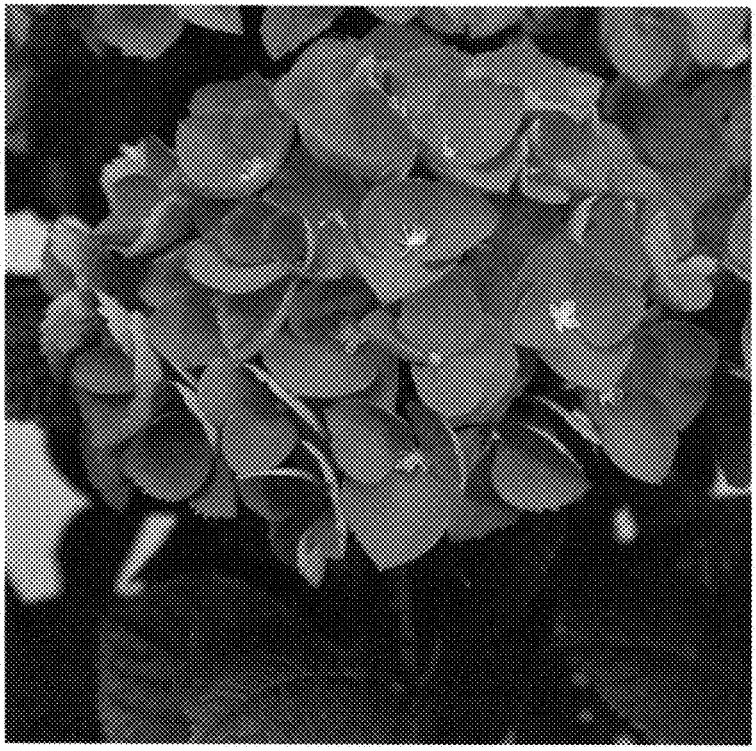

The photograph in FIG. 2 provides a close-up view of an inflorescence of 'HORTMADACE'.

Figure 3:
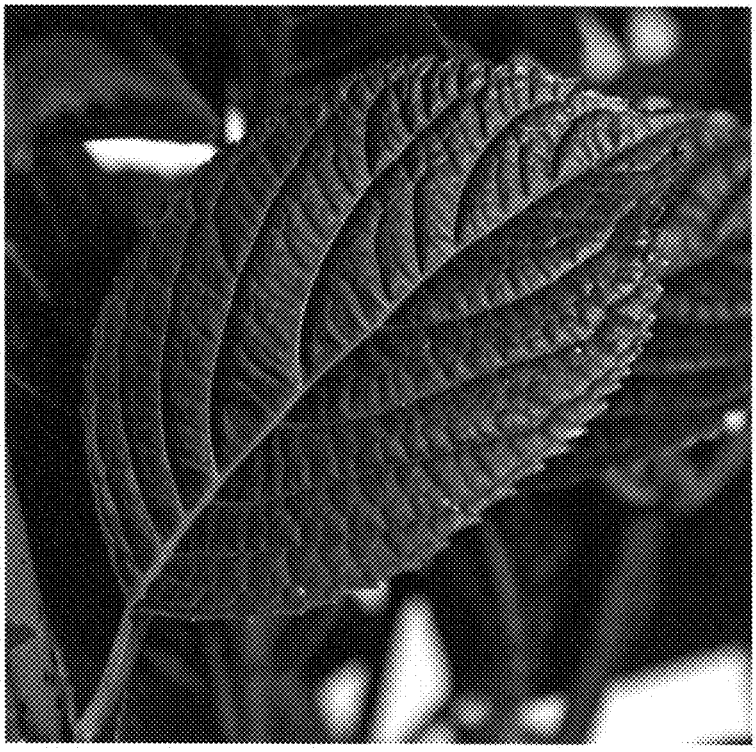

The photograph in FIG. 3 provides a close-up view of a leaf of 'HORTMADACE'.

The colors in the photographs may differ slightly from the color values cited in the detailed botanical description, which accurately describe the colors of the new *Hydrangea*.

BOTANICAL DESCRIPTION OF THE PLANT

The following is a detailed description of two year-old plants of 'HORTMADACE' as grown in a greenhouse in 1.5-liter containers in Boskoop, The Netherlands. Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Blooming period.*—Blooms from May to August as greenhouse grown plants in Boskoop, the Netherlands.

*Plant type.*—Deciduous shrub, mophead type *Hydrangea.*

*Plant habit.*—Broad upright.

*Height and spread.*—Reaches about 43.6 cm in height and 60 cm in spread in a 1.5-liter container and 1 m in height and 1 m in spread as grown in the landscape.

*Hardiness.*—At least in U.S.D.A. Zones 5 to 9.

*Diseases resistance.*—No particular susceptibility or resistance to diseases or pests has been observed.

*Root description.*—Fine and fibrous.

*Propagation.*—Softwood stem cuttings.

*Root development.*—An average of 6 months at average air temperatures of 15° to 25° C. to finish a young plant.

*Growth rate and vigor.*—Moderate.

Stem description:

*Stem shape.*—Rounded.

*Stem strength.*—Strong.

*Stem color.*—New growth; 144A, mature growth; 199C.

*Stem size.*—Average of 30.6 cm (excluding inflorescence) in length and 6 mm in diameter.

*Stem surface.*—Glabrous, moderately glossy, sparsely to moderately lenticellate, lenticles; 5 per $cm^2$, an average of 2.5 mm in length and 1 mm in width, 187A in color.

*Internode length.*—Average of 5.5 cm.

*Branching.*—Average of 11 lateral branches without pinching.

Foliage description:

*Leaf shape.*—Ovate to broadly ovate.

*Leaf arrangement.*—Opposite.

*Leaf division.*—Simple.

*Leaf base.*—Obtuse to short attenuate.

*Leaf apex.*—Apiculate.

*Leaf margins.*—Serrate.

*Leaf venation.*—Pinnate, upper surface color; 144B, lower surface color; 144B to 144C.

*Leaf size.*—Matures to an average of 10.2 cm in length and 6.8 cm in width.

*Leaf attachment.*—Petiolate.

*Leaf surface.*—Upper surface; glabrous, rugose and moderately glossy, lower surface; glabrous, rugose and matte.

*Leaf color.*—Young foliage upper surface; color between 143B and 144A, young foliage lower surface; 144B, mature foliage upper surface; a color between N137B and 139A, mature foliage lower surface; color between 143A and 147B.

*Petioles.*—An average of 1.7 cm in length and 4 mm in diameter, color; upper surface 144B and slightly tinged 182B, lower surface 144B, glossy surface.

Inflorescence description:

*Inflorescence type.*—Terminal panicle, mophead in form comprised of a center region of fertile flowers surrounded by single sterile flowers.

*Lastingness of inflorescence.*—Persistent, 4 months with pink-red coloration retained for about 6 weeks (depending on growing conditions).

*Lastingness as a cut flower.*—Pink-red color is retained for 2 weeks as a fresh cut and for several months as an aged dried flower.

*Inflorescence substance.*—Sturdy sterile flowers as the sepals do not turn upside down or brown with age.

*Inflorescence number.*—One per lateral or sublateral stem if pinched.

*Inflorescence size.*—Average of 11.6 cm in height and 16 cm in diameter.

*Flower number.*—Average of 70 sterile flowers and 15 fertile flowers per panicle.

*Flower fragrance.*—None.

*Flower aspect.*—Upright to outward.

*Flower size.*—Sterile flowers; an average of 4.4 cm in diameter and 2 cm in depth, fertile flowers; an average of 8 mm in diameter and 7 mm in depth.

*Flower type.*—Rotate.

*Flower buds.*—Sterile flowers; average of 8 mm in length and 7 mm in diameter prior to opening, obovate in shape, 145D in color, fertile flowers; average of 4 mm in length and 3 mm in diameter, broad obovate in shape, color; 70C, base 150D.

*Peduncles.*—Moderately strong, average of 4 cm in length and 2 mm in width, 186A in color, surface matte, and moderately covered with short soft hairs an average of 0.1 mm in length and width, too small to measure color.

*Pedicels.*—Sterile flowers; held at an average angle of 35° from vertical, an average of 3.8 cm in length and 1.25 mm in diameter, strong, 186A in color, surface matte, and moderately covered with short soft hairs an average of 0.1 mm in length and width, too small to measure color, fertile flowers; held at an average angle of 10° from vertical, an average of 5 mm in length and 1 mm in diameter, moderate strength, and moderately covered with short soft hairs an average of 0.1 mm in length and width, too small to measure color, 186C in color.

*Petals.*—Sterile flowers; average of 5, rotate in arrangement, ovate and moderately concave in shape, entire margin, acute apex, cuneate base, average of 4 mm in length and 3 mm in width, upper surface glabrous and matte, lower surface glabrous and slightly glossy, color of upper and lower surface when opening and when fully opened N66D, not fading, dropped shortly after maturity, fertile flowers; an average of 5, rotate arrangement, ovate to slightly concave apex, cuneate base, entire margins, ovate and slightly concave in shape, an average of 4 mm in length and 3 mm in width, upper and lower surface; glabrous and dull, color; upper and lower surface when opening and when fully open; N66D, color not fading, petals drop at maturity.

*Sepals.*—Sterile flowers; average of 4, rotate arrangement, reniform to broadly deltoid in shape, an average of 2.5 cm in length and 3 cm in width, broad bluntly acute apex, obtuse to very short broad attenuate base, upper surface slightly rugose, glabrous and matte, lower surface glabrous and matte, serrate margins, color when opening upper surface; N57A, 61B, 155A and 153D, lower surface; N57C to N57D, color when fully opened upper surface; 61B to 61C and lower surface; N57D, color fades to 183C to 183D on upper surface, color fades to 182A to 182B on lower surface, fertile flowers; 5, rotate in arrangement, ovate in shape, entire margin, acute apex, broad cuneate base, average of 1.5 mm in length and 1 mm in width, both surfaces are glabrous and matte, color of upper and lower surface when opening 144B, color of upper and lower surface when fully opened 144B to 144C.

Reproductive organs: (Present on fertile flowers and sterile flowers).

*Stamens.*—Sterile flowers; average of 8, anther is broad kidney-shaped, an average of 0.75 mm in length and 197B in color, filament is 3 mm in length and NN155A in color, pollen is moderate in quantity and 155A in color, fertile flowers; average of 8, anther is broad kidney-shaped, 0.75 mm in length and 197B in color, filament is 3 mm in length and NN155A in color, pollen is moderate in quantity and 155A in color.

*Pistils.*—Sterile flowers; average of 3, an average of 1.5 mm in length, stigma is club-shaped and 156D in color, style is an average of 0.5 mm in length and 155A in color, ovary is 155A in color, fertile flowers; average of 3, an average of 1.5 mm in length, stigma is club-shaped and 156D in color, style is an average of 0.5 mm in length and 75C in color, ovary is 155A in color.

*Fruit and seed.*—Has not been observed to date.

It is claimed:

1. A new and distinct cultivar of *Hydrangea* plant named 'HORTMADACE' substantially as herein illustrated and described.

* * * * *